US006579533B1

(12) United States Patent
Törmälä et al.

(10) Patent No.: US 6,579,533 B1
(45) Date of Patent: Jun. 17, 2003

(54) BIOABSORBABLE DRUG DELIVERY SYSTEM FOR LOCAL TREATMENT AND PREVENTION OF INFECTIONS

(75) Inventors: Pertti Törmälä, Tampere (FI); Esa Suokas, Tampere (FI); Hannu Aro, Turku (FI); Jyri Koort, Turku (FI)

(73) Assignee: Bioasborbable Concepts, Ltd., Tampere (FI)

( * ) Notice: Subject to any disclaimer, the term of this patent is extended or adjusted under 35 U.S.C. 154(b) by 0 days.

(21) Appl. No.: 09/449,667

(22) Filed: Nov. 30, 1999

(51) Int. Cl.$^7$ ............................. A61F 2/00; A61F 13/00; A61K 9/14; A61K 33/42; A61K 31/74

(52) U.S. Cl. ..................... 424/426; 424/422; 424/423; 424/601; 424/602; 424/489; 424/484; 424/78.08

(58) Field of Search .................. 424/426, 489, 424/484, 422, 78.08, 423, 601, 602

(56) References Cited

U.S. PATENT DOCUMENTS

| | | | |
|---|---|---|---|
| 3,887,699 A | * | 6/1975 | Yolles ........................ 424/19 |
| 4,347,234 A | | 8/1982 | Wahlig et al. |
| 4,610,692 A | | 9/1986 | Eitenmuller et al. |
| 4,612,923 A | | 9/1986 | Kronenthal |
| 4,853,225 A | | 8/1989 | Wahlig et al. |
| 4,968,317 A | | 11/1990 | Tormala et al. |
| 5,084,050 A | * | 1/1992 | Draenert ..................... 606/77 |
| 5,268,178 A | | 12/1993 | Calhoun et al. |
| 5,281,419 A | * | 1/1994 | Tuan et al. ................. 424/426 |
| 5,562,704 A | | 10/1996 | Tamminmaki et al. |
| 5,591,453 A | * | 1/1997 | Ducheyne et al. .......... 424/484 |
| 5,618,563 A | | 4/1997 | Berde et al. |
| 5,641,514 A | | 6/1997 | Cho |
| 5,676,699 A | * | 10/1997 | Gogolewski et al. ......... 623/16 |
| 5,709,875 A | | 1/1998 | Lebugle et al. |
| 5,756,127 A | | 5/1998 | Grisoni et al. |
| 5,876,446 A | | 3/1999 | Agrawal et al. |

FOREIGN PATENT DOCUMENTS

| | | |
|---|---|---|
| DE | 34 45 709 A1 | 6/1986 |
| EP | 014639 A2 | 6/1985 |
| EP | 0423155 B1 | 4/1991 |
| EP | 0449867 B1 | 10/1991 |
| EP | 0 475 077 B1 | 3/1992 |
| FI | 98136 | 1/1997 |
| FI | 100217 B | 10/1997 |
| WO | 89/00431 | 1/1989 |
| WO | 90/07304 | 7/1990 |
| WO | 90/12550 | 11/1990 |
| WO | WO 93 23094 A | 11/1993 |
| WO | 96/21628 | 7/1996 |
| WO | WO 00 13717 A | 3/2000 |

OTHER PUBLICATIONS

Vainionpaa et al., "Surgical Applications of Biodegradable Polymers in Human Tissues", Prog. Polym. Sci., vol. 14, 679–716, 1989.

Wei et al., "A Bioabsorbable Delivery System for Antibiotic Treatment of Osteomyelitis", J. Bone Joint Surg., vol. 73B, pp. 246–252; 1991.

Lin et al., "Evaluation of a Biodegradable Drug Delivery System for Chronic Osteomyelitis", 38th Annual Meeting, Orthopaedic Research Society, Feb. 17–20, 1992, p. 217.

Robinson et al., "Preparation and Degradation of a Biodegradable Gentamicin Delivery System for the Treatment of Osteomyelitis", 38th Annual Meeting, Orthopaedic Research Society, Feb. 17–20, 1992, p. 427.

Garvin et al., "Treatment of Canine Osteomyelitis with a Biodegradable Antibiotic Implant", 38th Annual Meeting, Orthopaedic Research Society, Feb. 17–20, 1992, p. 437.

Winckler et al., "A bioabsorbable drug delivery system for local treatment of osteomyelitis—polyglycolic acid/poly–L–lactid acid as a carrier", Langenbecks Arch Chir (1992) 377:112–117.

Teupe et al., "Ciprofloxacin–impregnated poly–L–lactic acid drug carrier", Arch Orthop Trauma Surg (1992) 112:33–35.

Yamada et al., "Creutzfeldt–Jakob Disease Transmitted by a Cadaveric Dura mater Graft", Neurosurgery, vol. 34, No. 4, Apr. 1994, pp. 740–744.

Galandiuk et al., "Absorbable, Delayed–Release Antibiotic Beads Reduce Surgical Wound Infection", The American Surgeon, vol. 63, No. 9, Sep. 1997, pp. 831–835.

Stoor et al., "Antibacterial effects of a bioactive glass paste on oral microorganisms", Acta Odontol Scand 56 (1998), pp. 161–165.

Dahl et al., "Acute Osteomyelitis in Children: A Population–based Retrospective Study, 1965 to 1994", Scand J Infect Dis 30: 573–577, 1998.

Ueng et al., "Management of Femoral Diaphyseal Infected Nonunion with Antibiotic Beads Local Therapy, External Skeletal Fixation, and Stage Bone Grafting", The Journal of Trauma Injury, Infection and Critical Care, vol. 46, No. 1, Jan. 1999, pp. 97–103.

Di Silvio et al., "Biodegradable drug delivery system for the treatment of bone infection and repair", Journal of Materials Science: Materials in Medicine 10 (1999) 653–658.

(List continued on next page.)

Primary Examiner—James M. Spear
Assistant Examiner—Blessing Fubara
(74) Attorney, Agent, or Firm—Kenyon & Kenyon

(57) ABSTRACT

This invention relates to bioabsorbable materials and implants used to prevent and treat infection and promote bone growth. More specifically, this invention relates to synthetic bioabsorbable drug delivery materials and implants comprising: (a) a synthetic bioabsorbable polymeric matrix; (b) an antibiotic phase dispersed into said polymeric matrix; and (c) antibacterial, bioabsorbable, bioactive glass, dispersed into said polymeric matrix for the promotion of bone growth.

15 Claims, No Drawings

OTHER PUBLICATIONS

Domb et al., "Polyanhydrides as Carriers of Drugs", Biomedical Polymers, Chapter 3, pp. 69–96.

Brink, "Bioactive Glasses with a Large Working Range" (1997).

Rokkanen et al., Absorbable Fixation in Orthopedic Surgery (AFOS)—Surgical Technique, Helsinki University, Helsinki (1996).

Rokkanen et al., "Traumatologia" (Traumatology), Kandidaattikustannus Oy, Helskinki, Finland (1995), pp. 103–104.

Soriano et al. "Formulation of Calcium Phosphate/poly (d,L–lactide) blends containing Gentamycin for Bone Implantation"; J. Controlled Release, vol. 68, Jul. 2000, pp. 121–134.*

Soriano I et al: "Formulation of Calcium Phosphates/Poly (d, 1–lactide) Blends Containing Gentamicin for Bone Implantation"; Journal of Controlled Release, Elsevier Science Publishers B.V., vol. 68, Jul. 2000 (2000–07), pp. 121–134.

Radin S et al: "Calcium Phosphate Ceramic Coatings as Carriers of Vancomycin" Biomaterials, GB, Elsevier Science Publishers BV., Barking, vol. 18, No. 11, Jun. 1, 1997 (Jun. 1, 1997), pp. 777–782.

International Search Report for corresponding International Application PCT/EP00/11947, Feb. 28, 2001.

* cited by examiner

BIOABSORBABLE DRUG DELIVERY SYSTEM FOR LOCAL TREATMENT AND PREVENTION OF INFECTIONS

FIELD OF THE INVENTION

This invention relates to methods of preventing and treating infections. More specifically, it relates to the use of synthetic, bioabsorbable polymer-based composite materials and implants, like microspheres, membranes, capsules, shells, honeycombs, spheres, rods, screws, plates, suture anchors, tacks, and other fixation devices, which contain (a) a bioabsorbable polymer, copolymer or polymer alloy ("polymeric") matrix, (b) an antibiotic or antibiotic mixture dispersed into the matrix and (c) a bioactive glass filler or reinforcement dispersed in the matrix, which bioactive glass phase promotes bone growth and possesses an antibacterial effect. Preferred embodiments of the materials and implants of the present invention provide a sustained release of antibiotic over several weeks or months for the prevention and/or treatment of infection and also can facilitate new bone formation, fracture healing, and/or endoprosthesis attachment. These implants may be effectively implanted into or on (1) an infected bone, (2) a possibly infected defect, void or fracture in bone tissue, or (3) a bone, bone defect, void, fracture or on an endoprosthesis of a patient who has a risk of developing an infection in the treated bone.

BACKGROUND

Virtually all surgical procedures create some type of void or dead space within the patient's body. This is particularly true in the case of surgery to remedy a localized infection. The infected area—an area of relative tissue ischemia—must be debrided and filled in. Further, antibiotics must be administered to prevent recurrence of infection in the void. Thus, the materials of the present invention will have beneficial application in many different types of surgeries.

One example is chronic bone infection (osteomyelitis). The standard therapy includes debridement and sequestrectomy of infected, dead bone, followed by several weeks of intravenous antibiotics. Unfortunately this treatment has several drawbacks. The multiple doses of antibiotics that are needed can become quite expensive. Also, the intravenous or GI tract administration of antibiotics does not allow the antibiotic to be specifically directed to the location of the infection. Further, intravenous administration of antibiotics requires an operation for placement of a catheter, which can lead to serious complications. Additionally, the removal of infected bone leaves a void or gap in the bone tissue. If the gap is large it rarely ossifies, instead filling with connective tissue which can lead, in the worst case, to an increased risk of bone fracture. Also in the case of bone fractures, especially severely comminuted, possibly infected fractures, the poor ossification of fractured bone can lead to non-union and/or to other complications. Similar problems of infections and poor bone formation can occur in the case of endoprosthesis attachment.

There are many different materials, devices and techniques for the local prevention and treatment of infections.

A well-known procedure for the treatment of bone infections is the use of polymethymethacrylate (PMMA) beads that contain antibiotics (e.g. Septobal® beads). Such beads are placed in surgical voids and thereby fill the voids, as well as providing local bactericidal levels of antibiotic. However, even these PMMA beads have disadvantages. First, they usually can only provide bactericidal levels of antibiotic for about a few weeks, so patenteral antibiotic must also be given. Second, the PMMA beads must eventually be removed surgically, resulting in further trauma to the patient's body. Third, PMMA beads do not facilitate new bone formation. As an alternative to the PMMA beads, antibiotics have been mixed with a PMMA bone cement. However, this system also has the limitations which result from the use of a nonabsorbable biomaterial.

Fracture fixation devices, which can contain and release antibiotics, were first described in the late 1980's. For instance, U.S. Pat. No. 4,610,692 describes a method of producing sintered tricalcium phosphate implants for filling bone cavities and for fixing bone fragments in a living body, which comprises:

mixing tricalcium phosphate with at least one substance which forms a gas a high temperatures, shaping the thus-formed mixture into shaped bodies, baking the shaped bodies at a temperature sufficiently high to cause gas formation from said substance, thereby forming pores in said shaped bodies, impregnating said shaped porous bodies with a therapeutically-active ingredient, thereby distributing the same in the pores, and coating at least a portion of one of said shaped, porous bodies having said therapeutically-active ingredient distributed therein, with a coating of a predetermined thickness of a biodegradable substance, whereby the time of absorption of said therepeutically-active ingredient is controlled by the thickness of said biodegradable substance.

However, such sintered ceramic bodies are brittle and mechanically weak, which is a disadvantage when such materials are used to manufacture implants for the fixation of bone fragments. Additionally, the biodegradable coating on the porous body prevents bone growth into the pores of the tricalcium phosphate body. Therefore, there is not an advantageous synergism caused by the simultaneous release of antibiotic and the growth of bone tissue. Also, the therapeutically-active ingredient (like antibiotic) is not mixed with a bioabsorbable matrix, but rather is distributed among the pores within the tricalcium phosphate body.

FI 83729 describes bioabsorbable bone fracture fixation implants (external fixator pins and half-pins) and their coatings, which are manufactured of a bioabsorbable polymer, copolymer, polymer alloy or composite, which pin or coating includes an antibiotic or antibiotic mixture which is released from the surface of pin or coating.

PCT/FI 88/00108 describes absorbable, self-reinforced polymeric materials and absorbable fixation devices for the fixation of various tissues or parts of tissues to each other by techniques of internal fixation or external fixation. Typical devices described are rods, plates, screws, nails, intramedullary rods, clamps, cramps etc., which can be applied in internal and/or external fixation of bone fractures, osteotomies, arthrodeses, joint damages and/or of cartilage tissue. Also disclosed are staples, clamps, plates, cramps and corresponding devices, which can be applied in the fixation of soft tissues, fasciae, organs, etc. to each other. It is disclosed that these materials can contain different additives, like antibiotics.

U.S. Pat. No. 4,853,225 describes a method of combating an infection in a patient, where a medicament depot is implanted in the patient, the medicament depot consisting of a physiologically acceptable excipient, which achieves delayed release of at least one chemotherapeutic gyrase inhibitor as the active agent. However, synthetic bioabsorbable polymers are not used as the drug-releasing matrix (excipient), but rather as bioabsorbable binders of collagen, which as a material of biological origin has aroused concern of risks of microbial contamination. Also, this patent does not describe antibacterial bioactive glasses as a component of the excipient to promote bone growth.

PCT/FI 90/00113 describes polymeric, self-reinforced, absorbable surgical materials and/or implants, which can be implanted into or onto tissue, e.g., to repair tissue damage, to join tissues or their parts to each other, to augment tissues or their parts, to separate tissues or their parts from each other and/or from their surroundings, and/or to conduct material between tissues or their parts and/or out of tissues or from the outside into the tissues, where the reinforcing elements are wound at least partially around some axis penetrating the implant. It is also disclosed that these devices can contain some antibiotic.

PCT/FI 89/00236 describes a polymeric (absorbable or biostable) multilayer plate for the fixation of bone fractures, osteotomies, arthrodeses, or for the fixation of a ligament, tendon or connective tissue to the bone. The multilayer plate comprises at least two essentially superimposed polymer plates, which can include an antibiotic.

U.S. Pat. No. 4,347,234 describes a collagen-based drug delivery implant which, upon implantation, essentially maintains its shape and effects a retarded liberation of the drug. The implant comprises 0.2–20 weight percent of a pharmacoligially active drug material, 1–25 weight percent of a bioresorbable binding agent for collagen, and the balance being finely ground collagen. The binding agent consists essentially of a co- or homopolymer of natural amino acids or of hydrolyzed collagen or hydrolyzed elastin. The drug delivery implant further may comprise 0.1–40% by weight of a resorbable mass of calcium phosphate (to stimulate the growth of bone). Such biological tissue-based biomaterials create the risk of delivering host-based diseases, like viral or prior infections, into the human patients (see e.g. S. Yamada et al. Neurosurgery, 34 (4) 1994, p. 740–743).

Bioabsorbable polymeric drug delivery systems for the treatment of chronic osteomyelitis were described further in 1991–1992 by several groups. C. Teupe et al., in "Ciprofloxacin-impregnated poly-L-lactic acid drug carrier", Arch. Orthop. Trauma Surg. 112 (1992) 33–35 and S. Winckler et al., in "Resorbierbare Antibiotikumträger zur lokalen Behandlung der chronischen Osteitis—Polyglykols äure/Poly-L-Laktid als Träger, Experimentelle Untersuchungen in vitro", Langenbecks Arch. Chir. 377 (1992) 112–117, describe bioabsorbable polyglycolic acid (PGA) and poly-L-lactic (PLLA) cylinders containing the antibiotic ciprofloxacin, which is released from the cylinders in vivo during several weeks.

Bioabsorbable drug delivery systems were also described by Lin et al., "Evaluation of a biodegradable drug delivery system for chronic osteomyelitis," 38th Annual Meeting, ORS, Washington D.C., Feb. 17–20, 1992; Robinson et al. "Preparation and degradation of a biodegradable gentamycin delivery system for the treatment of osteomyelitis", 38th Annual Meeting, ORS, Washington D.C., Feb. 17–20, 1992; Garvin, et al., "Treatment of Canine Osteomyelitis with a Biodegradable Antibiotic Implant." 38th Annual Meeting, ORS, Washington D.C., Feb. 17–20, 1992; and Wei et al., "A bioabsorbable delivery system for antibiotic treatment of osteomyelitis," J. Bone Joint Surg. 73B (1991) 246–252.

U.S. Pat. No. 5,268,178 describes bioabsorbable antibiotic implants comprising at least one antibiotic drug. U.S. Pat. No. 5,281,419 describes an antibiotic-impregnated fracture fixation device and an antibiotic-impregnated drug delivery polymer.

Di Silvio and Bonfield describe a drug delivery system comprising gelatin for the combined release of therapeutic levels of both gentamicin and growth hormone in "Biodegradable drug delivery system for the treatment of bone infection and repair", Int. Conf. Adv. Biomater. and Tissue Eng., June 14–19, Capri, Italy, Book of Abstracts, 1998, p. 89–90. This system releases gentamicin only up to 14 days, which is in many cases too short of a time because effective healing of an osteomyelitis may need antibiotic treatment for at least several weeks (see e.g. L. Dahl et al, Scand. J. Infect. Dis., 30 (6), (1998) p. 573–7 or S. Veng et al., J. Trauma, 46 (1) (1999) p. 97–103). Additionally gelatine based systems are mechanically weak and cannot be used in the form of bone fracture fixation implants. Also animal-based biomaterials, like gelatin, have aroused concern of the risk of delivering animal-based diseases, like viral infections, into human patients. Also, the release of bone growth promoting factor (growth hormone) was limited to 2 weeks, which is far too short time for proper new bone formation, which in the case of cancellous bone is at least 6 weeks.

A. J. Domb et al. describes a bioabsorbable polyanhydride-based drug delivery system, the Septacin implant, for the treatment of chronic osteomyelitis. The Septacin implant is manufactured as a flexible chain of beads, consisting of a copolymer of fatty acid dimer (FAD) and sebacic acid, which is loaded with gentamicin (A. J. Domb et al., "Polyanhydrides as Carriers of Drugs" in "Biomedical Polymers" (S. W. Shalaby, Ed.), Hanser Publishers, Munich, 1994, p. 69–96). It was claimed that the beads, combined with adequate debridement, appear to be a clinically useful delivery system that may be used in the treatment of osteomyelitis and other soft tissue infection. However, there was no evidence of any osteopromoting (osteoconductive and/or osteoinductive) effects of Septacin beads.

S. Galandiuk et al. describes PGA beads containing either minocycline or amikacin and claims that delayed-release, absorbable, antibiotic-containing PGA beads effectively prevent infection in contaminated wounds and have the advantage of not requiring vehicle removal (63 American Surgeon 831–835 (1997)).

U.S. Pat. No 5,641,514 describes cement beads for orthopaedic surgery, manufactured from a mixture of antibiotics and cement. However, the cement beads are neither bioabsorbable nor osteopromoting, requiring a removal operation and replacement by fresh bone grafts.

U.S. Pat. No. 5,709,875 describes a material which can be implanted that may comprise an active substance in order to achieve a therapeutic effect of prolonged duration. This material comprises (a) a calcium phosphate with apatitic or triclinic structure comprising $HPO_4$ and $PO_4$ groups, (b) a biodegradable oside or polyoside, in particular dextran, (c) if required, an active substance comprising amine groups such as netilmicin and/or gentamicin sulphate. However, this patent does not show if the described material is effective in prolonged treatment (healing) of osteomyelitis. On the contrary, the described materials rapidly release a high amount of loaded antibiotic: 30%–60% release in 50 hours, which may cause disadvantageously high local antibiotic concentrations and compromise the long-term release of antibiotic in concentrations needed for the healing of osteomyelitis.

U.S. Pat. No. 5,756,127 describes a bioresorbable string of implantable beads in which the beads consist essentially of calcium sulphate and a quantity of a drug suitable for treating tissue disorders (bone infection), and in which both the beads and the line that joins the beads together are bioresorbable. However, although matrices based on calcium sulphate are biodegradable their rate of degradation is fixed and cannot be adapted to the rate of regeneration of the tissue in question and their degradation is generally too rapid for bony tissues. Therefore their use frequently entails the occurrence of "defects" in said tissues. They also have the disadvantage of not promoting regeneration of the tissue (see e.g. U.S. Pat. No. 5,709,875).

U.S. Pat. No. 5,876,446 desribes a biodegradable composition, to be included into surface pores of metallic press fit prosthetic devices, said biodegradable composition including a biodegradable polymer or ceramic matrix, said matrix further containing a pharmacologically active substance. However, U.S. Pat. No. 5,876,446 does not describe a combination of a biodegradable, drug-releasing polymer and biodegradable, antibacterial, osteoconductive ceramic.

Because the ceramic components of prior art materials are not bacteriocidic, there may be a risk that bacteria can adhere to the exposed surfaces of such ceramic particles. Therefore, it is advantageous for the ceramic component to be antibacterial.

The prior art does not describe totally synthetic bioabsorbable, antibiotic-releasing implants, which can release antibiotic in therapeutic doses over several weeks or months and which additionally show osteopromoting and bacteriocidic effects by incorporating a bioabsorbable, bioactive glass component to promote new bone formation over several weeks or months after a surgical operation.

Thus, a long-standing need exists for improved methods of preventing and treating infections in bone voids, bone fractures and endoprosthesis surgery.

In particular, a long-standing need exists for improved synthetic, bioabsorbable drug-releasing (antibiotic-releasing) implants which can prevent and/or treat infections, as well as promote new bone growth, in bone voids, bone fractures and on endoprostheses fixed in or on bone.

SUMMARY OF THE INVENTION

This invention describes novel, synthetic bioabsorbable drug delivery materials and implants that are appropriate for use with compromised bone or with other musculoskeletal tissue, for example with infected and/or fractured bone and at bone-endoprosthesis boundary. The drug delivery materials and implants of the present invention comprise (a) a synthetic bioabsorbable polymeric (polymer, copolymer or polymer alloy) carrier into which is dispersed, mixed, dissolved, homogenized, and/or covalently bound ("dispersed") (b) an antibiotic or antibiotic mixture, effective for the treatment and/or prevention of infection (such as osteomyelitis) over several weeks or months and (c) a bone growth promoting, antibacterial bioactive glass particle or fiber filler or reinforcement, effective for promoting new bone formation for several weeks or months after a surgical operation. The drug delivery materials and implants of the present invention can be in any appropriate form into which the polymer matrix, including antibiotic(s) and ceramic particle and/or fiber phase, can be formed with polymer technological processing methods.

The drug delivery materials and implants of the invention can also contain surface or inner porosity to facilitate new bone growth.

One particular advantage of the bioabsorbable drug delivering fixation implants of the present invention is that they may be used (1) for the reduction of compound fractures, (2) for the prevention and/or treatment of infection and (3) for promotion of new bone formation into the bone area, where the infection has destroyed bone.

Another advantage of the bioabsorbable drug delivery implants of this invention is that they can be used in the fixation of bone fractures and/or osteotomies in patients who have a high risk of developing infections after operation. Such patients are, e.g., patients with diabetes or patients with poor blood circulation in their extremities.

Also provided herein are methods for forming the bioabsorbable drug delivery materials of this invention and methods for using the same.

DETAILED DESCRIPTION OF THE INVENTION

Bioabsorbable drug delivery materials and implants of the present invention comprise:

(a) a synthetic bioabsorbable polymeric (a polymer, a copolymer or polymer alloy) matrix, (b) an antibiotic phase (preferably 1 to 20 w/w %) dispersed into the polymeric matrix, and (c) an antibacterial particle and/or fiber phase of bioactive glass, dispersed into and/or on the polymeric matrix that promotes bone growth.

Also, in a preferred embodiment of the present invention, the materials and implants have surface porosity and/or inner porosity to further promote bone growth.

The drug delivery materials and implants of the present invention can be in any appropriate form into which the polymer matrix, including antibiotic(s) and ceramic particle and/or fiber phase, can be formed with polymer technological processing methods. Typical forms are microparticle suspensions, sprays, powders, pastes, microcapsules, capsules, tablets, spheres, cylinders, beads, beads on a string, short or long fibers or fiber constructions, like threads, cords, fabrics, meshes, non-woven felts, laminates or membranes and polymeric films. The materials and implants of the present invention may also be in the form of bone fracture fixation implants, like pins, screws, plates, tacks and intramedullary nails or soft-tissue-to-bone fixation implants, like screws, tacks, bolts, suture anchors, tissue anchors, interference screws and wedges, or soft tissue devices like arrows. Further, an implant of the present invention may be created by coating a fracture fixation implant or an endoprosthesis with a coating of an antibiotic and a ceramic filler dispersed and/or dissolved into a bioabsorbable polymer. The drug delivery materials of the invention may also be formed into fixation devices and guided tissue regeneration devices, like pins, rods, screws, plates, membranes, meshes, tacks, bolts, intramedullary nails, clamps, arrows, or other devices which are used in bone-to-bone or soft tissue-to-bone fixation and whose geometries are described extensively in the literature, e.g. in U.S. Pat. No. 4,968,317, EPO Patent No. 0423155, EPO Patent No. 449867, U.S. Pat. No. 5,562,704, FI Patent No. 98136, and in references mentioned in the above patents.

The bioabsorbable polymeric matrix of the drug delivery systems of the invention can be selected from a variety of synthetic bioabsorbable polymers, which are described extensively in the literature. Such synthetic bioabsorbable, biocompatible polymers, which may release antibiotic(s) over several weeks or months and which may also act as suitable matrices for bioabsorbable antibacterial particle and/or fiber fillers or reinforcements of bioactive glass, can include poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants of the present invention are mentioned e.g. in U.S. Pat. Nos. 4,968,317, 5,618,563, FI Patent No. 98136, FI Patent No. 100217B, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated. For treating bone fractures, bone infections and other slow healing wounds, a bioabsorbable polymer with a slower degradation time is preferred, as that will provide for the release of antibiotics and bacteriocidal bioactive glass at the wound cite over a longer period of time.

Variations in the composition of each of the materials of the system, such as the type and molecular weight of the polymer matrix, and the relative proportion and amount of antibiotic, affect the release rate of the antibiotic, and therefore allows the rate to be modified to meet the requirements of different treatment situations. In general, the lower the molecular weight of the bioabsorbable material the faster it will biodegrade and release drugs. In a preferred embodiment of the present invention, antibiotics are released over several weeks or months.

A variety of antibiotics can be used in the materials and implants of the present invention for the treatment and/or prevention of infection. Suitable antibiotics include many classes, such as aminoglycoside antibiotics or quinolones or beta-lactams, such as cefalosporines, e.g., ciprofloxacin, gentamycin, tobramycin, erythromycin, vancomycin, oxacillin, cloxacillin, methicillin, lincomycin, ampicillin, and colistin. Suitable antibiotics have been described in the literature (see e.g. P. Rokkanen et al. "Traumatologia" (Traumatology), Kandidaattikustannus Oy, Helsinki, Finland, 1995, p. 103–104).

A variety of bioabsorbable, bone-growth-promoting, bacteriocidic, bioactive glasses can be added into or on the bioabsorbable polymers in manufacturing the materials and implants of the present invention. Appropriate bioactive glasses have been described in, e.g., EPO Patent Appl. 0 146 398, U.S. Pat. No. 4,612,923, and in PCT patent application WO 96/21628, M. Brink, "Bioactive Glasses with a Large Working Range", Doctoral Thesis, Åbo Academi, Turku, Finland, 1997, P. Stoor et al. "Antibacterial effects of a bioactive glass paste on oral micro-organismus", Acta Odontol. Scand. 56 (1998) 161–165, and in references cited therein. These bioactive glasses can express antibacterial effects and enhance bone growth when used as components of bioabsorbable drug-releasing polymeric materials and implants of this invention.

The bioactive glasses may be incorporated into the materials and implants of the present invention as particle fillers, short fiber reinforcements (fiber lengths preferably between 1 μm–10 mm), or as long fibers or filaments or fabrics made of such fibers. Particles or short fibers of bioactive glass are especially advantageous fillers and/or reinforcements in bioabsorbable polymers because as they slowly dissolve in vivo they cause an antibacterial effect and form hydroxyapatite precipitations, (see e.g. M. Brink, "Bioactive glasses with a large working range", Doctoral Thesis, Åbo Akademi University, Turku, Finland, 1997) which enhance the new bone growth with and along the surface of the materials and implants of the present invention.

There are several methods available to manufacture the drug delivery materials and implants of the present invention. The raw materials (bioabsorbable polymer(s), antibiotic(s) and bioactive glass filler or fiber reinforcement) can initially be in the form of powders, granules, flakes, fibers, or other particle forms and can be mixed together mechanically. The mechanical mixture can be heated and processed using known methods of polymer technology. These include using a batch mixer (e.g. by a Brabender-, Banbury-, Farrel- or Sigma-type mixer), a continuous extrusion process using e.g. a single- or twin-screw extruder or a special conical screw extruder, and injection molding, compression molding or ultrasonic compression so that the polymeric matrix melts or softens and the antibiotic phase and ceramic particle and/or fiber phase are dispersed into the polymer matrix. Such a dispersion can be pelletized or granulated in the melt state or after cooling (e.g. to room temperature).

In another preferred embodiment of the present invention, the material can be crushed at room temperature or after additional cooling (e.g. with liquid nitrogen). The crushed powder can be separated, e.g., sieved, to particles of the desired size. The small particles (e.g., diameter<10 $\mu$m, 10–50 $\mu$m or 50–100 $\mu$m) can be used as powders or as microparticle suspensions in suitable solutions, like in distilled water, saline, oils, etc. Such suspensions can be easily injected into infected tissue areas and/or into bone gaps. In another preferred embodiment of the present invention, these powder-like systems can be used also as sprays, powders and as pastes, when mixed e.g. with suitable lotions, creams, oils, etc. In yet another preferred embodiment of the present invention, the porous surfaces of non-cemented endoprostheses (like hip prostheses) can be impregnated and/or coated with such powders or suspensions before installation of prosthesis. Such powders or suspensions of the present invention, when impregnated into the pores of endoprostheses prevent development of infections and also promote new bone formation into the pores, thereby facilitating and accelerating the development of bony union between the endoprosthesis and the surrounding bone.

In other embodiments of the present invention, manufacturing possibilities include composite fabrication techniques, like lamination, film stacking, injection, powder impregnation, co-weaving and knitting, pultrusion and filament winding of polymer matrix, antibiotic, and bioactive fibers or fiber fabrics to obtain high-strength, antibiotic releasing, antibacterial, osteopromoting bioabsorbable materials.

In another preferred embodiment, the drug releasing material and implants of the present invention can also be applied in the form of spheres, cylinders, ellipsoids, etc. (diameter or dimensions preferably between 1–7 mm), which can be manufactured from melt molded polymer-antibiotic-ceramic mixture e.g. with extrusion (followed by mechanically cutting the extrudate) or with injection molding. Such "macroscopical" particles can be used to fill infected and purified bone defects, holes and gaps. In another preferred embodiment of the present invention, they can also be combined with gels (which optionally may contain bone growth factors (BMP)), lotions, or pastes etc. to facilitate the new bone formation effect and/or to make the handling of system more easy.

In still another embodiment, the materials or implants of the present invention can be applied in the form of beads and/or cylinders that are bound to each other with a bioabsorbable mono- or multifilament wire to make pearl-like systems to be located inside of bone defects.

In another embodiment, the drug releasing materials of the present invention can also be spinned to fibers either with melt spinning or with spinning of polymer solutions containing antibiotic and ceramic particle suspension. Such fibers can be used as drug releasing implants of the present invention in the form of cut fibers, threads, cords, knitted or woven fabrics, meshes, non-woven felts, laminates or membranes. Such fiber constructions can be used conveniently to fill and/or to cover infected and purified bone gaps, voids or fractures in order to guide and intensify new bone formation.

According to another preferred embodiment, the drug releasing materials and implants of the present invention can be applied in the form of fixation devices, like bone fracture or osteotomy fixation pins, rods, screws, plates, tacks, bolts, wedges, intramedullary nails or soft tissue-to-bone fixation tacks or suture anchors etc. Such tissue fixation implants are especially advantageous, because in addition (a) to promoting tissue healing by physically holding the damaged tissue, they (b) prevent and treat infections and also (c) promote new bone formation, e.g., into drill holes, because the bioactive bioabsorbable ceramic, released by the bioabsorption of the polymer matrix, facilitates new bone formation. Such tissue fixation implants can be manufactured of matrix polymer(s) and antibiotic(s) and bioactive glass particle filler(s) and/or fiber or fabric reinforcement(s), or of pellets or granules made of them, with polymer processing methods, like continuous compounding extrusion, injection molding, compression molding or pultrusion. Preforms, made with the above methods, can also be oriented and self-reinforced by solid state deformation, like by drawing, shearing, compression, rolling, by hydrostatic extrusion or ram extrusion.

Self-reinforced, drug releasing tissue fixation implants of the invention are especially advantageous in the treatment of infected bone fractures and open bone fractures, because self-reinforced implants of the invention have much higher strength values than the corresponding non-reinforced, thermally melted bioabsorbable implants (see e.g. S. Vainionpää et al., "Surgical Applications of Biodegradable Polymers in Human—Tissues" Prog. Polym. Sci., Vol. 14, 1989, 679–716). High strength makes the self-reinforced drug-releasing materials and implants of the present invention more safe and versatile as fixation implants than traditional drug-releasing implants, e.g. those described in U.S. Pat. No. 5,281,419. Additionally, the self-reinforced drug-releasing implants of the present invention facilitate new bone formation in the fracture area and in drill hole(s) in bone by the effect of the bioabsorbable, bioactive glass particles and /or fibers.

The drug-releasing materials of the present invention can also form one part of a composite fixation implant system, where part of the implant system is not drug-releasing. For instance, the drug-releasing materials of the present invention may be applied to or coated on a fracture fixation implant, like a bioabsorbable plate, pin, screw or nail. In another embodiment of the present invention, an intramedullary nail comprising a bioabsorbable or metallic rod with a concentric layer of the drug-releasing and new bone formation promoting material of the present invention coated thereon, may be inserted intraosseously by techniques known in the art to repair an open tibial fracture. In yet another embodiment, a layer of the drug-releasing material of the invention may be coated on a fracture plate which can be used in fracture fixation by techniques known in the art.

The fracture fixation implants of the present invention may also contain at their surface pores, holes, small gaps, longitudinal or spirally oriented grooves, hollows, etc. into which the drug-releasing and new bone formation promoting material of the invention can be spreaded, pressed or melt molded.

The following, non-limiting examples further illustrate the present invention.

EXAMPLE 1

Ultrasonical Molding of Antibiotic-releasing, Bioabsorbable Spheres for Treatment of Osteomyelitis Vacuum dried poly(DL-lactide) homopolymer (racemic PDLLA with 50% D-lactide and 50% L-lactide monomers) powder ($M_w$=133,200, manufacturer: Boehringer Ingelheim, Germany), bioactive, antibacterial glass 13 particles, i.e., spheres (size range 90 μm–125 μm, manufacturer: Abmin Technologies Oy, Finland) and dried ciprofloxacin powder (manufacturer: China Jiangsu International Economic and Technical Cooperation Corporation, China) were mixed manually. The weight composition of mixture was: PDLLA 56 (w/w), bioactive glass 36 (w/w), and ciprofloxacin 8 (w/w). Spheres with diameter of 2 mm were made of the powder mixture by ultrasonic molding (according to EP 0676956 B1) in a two-piece mold with 5 spherical cavities (r=1 mm), using RINCO Ultrasonics MP201 welding device (manufacturer: RINCO Ultrasonics AG). Welding parameters were: welding time 0.5 s, pressure approximately 1.0 bar and energy per sample 150 Ws. The beads (spheres) were dried and packed into Al-foil pouches, which were closed and sterilized with gamma-radiation with the dosage of 2.8 Mrad.

The release of ciprofloxacin from the sterile composite beads was studied in phosphate buffer (pH 7.4 at 37° C.), according to methods of C. Teupe et al. Arch. Orthop. Trauma. Surg. 112 (1992) p. 33–35. The test time was 4 weeks. The release of ciprofloxacin from composite spheres was initially high (>100 mg/l) and decreased progressively to the level of about 10 mg/l in 4 weeks. The minimum inhibition concentration (MIC) of most microbial strains is <2 mg/l. Therefore, these composite spheres can be used effectively in treatment and prevention of osteomyelitis.

It is natural that the size and geometry of the implants for treatment of osteomyelitis, as described in this example, is not limited to spheres or beads, but can be formed into other sizes and/or geometries, like microspheres, capsules, tablets, pearls, pearls in string, membranes or films, fibers, filaments, cords or knitted or woven or nonwoven fiber fabrics.

EXAMPLE 2

Clinical Applications of Bioabsorbable, Ciprofloxacin Releasing, Osteoconductive Spheres The present example is provided to outline a preferred proposed use of the drug delivery implants of the present invention in the form of spheres in treatment of osteomyelitis and in promotion of new bone formation in human patients.

An osteomyelitis colony in a bone of a human patient would be purified by removing the infected tissue. The bone void created by purification of the infected tissue would then be filled with sterile beads described in EXAMPLE 1 using techniques well known to those of skill in the surgical art.

It is expected that the bioabsorbable, ciprofloxacin-releasing, antibacterial, osteopromoting, bioactive glass-containing beads will (a) provide effective release of ciprofloxacin for several weeks into the bone surrounding the void to treat and/or prevent infection and (b) facilitate new bone formation into the void and (c) express additional antibacterial effect by means of bioabsorbable, bioactive glass particles (spheres) up to several months.

EXAMPLE 3

Manufacturing of Antibiotic-releasing, Self-reinforced, Bioabsorbable, Antibacterial, Osteoconductive Screws for Fixation of Infected Cancellous Bone Fractures and of Fractures in Patients with High Risk of Infection.

Vacuum dried poly-L/DL-lactide (P(L/DL)LA) 70/30 (Resomer® LR 708 (inh. viscosity 5.5 dl/g; manufacturer Boehringer Ingelheim, Germany)) was mixed mechanically with 30% (w/w) of bioactive glass 13–93 spheres (size distribution 50–125 μm), and 6% (w/w) of ciprofloxacin. The mixture was melt extruded into a cylindical bar of diameter 7 mm. Nitrogen atmosphere was used in extruder hopper to avoid air contact.

The cylindical extrudate rods were precooled with $N_2$ blow and led to a transportation band for cooling to room temperature. Extruded P(L/DL)LA-bioactive glass-ciprofloxacin composite rods were self-reinforced by solid state die-drawing process at 95° C. The draw ratio 3 was used.

The self-reinforced rods (billets) were processed further to screws with the length of 40 mm and maximum thread diameter of 3.5 mm by turning the threads on the rods by a lathe and by compressing the screw head to the other end of the billet in a heated mold. The geometry of the screws was the same as that of a commercial Bionx Smart Screw™. The screws were dried in vacuum, packed into Al-foil pouches in dry $N_2$-atmosphere and sterilized with gamma radiation with the dosage of 2.8 M Rad.

EXAMPLE 4

Clinical Applications of Antibiotic-releasing, Self-reinforced, Bioabsorbable, Antibacterial, Osteoconductive Screws for Fixation of Infected Cancellous Bone Fractures and of Fractures in Patients with High Risk of Infection.

The present example is provided to outline a preferred proposed use of the ciprofloxacin-releasing, self-reinforced, bioabsorbable, antibacterial, osteoconductive screws of the present invention (a) in fixation of infected fractures and of fractures in patients with high risk of infection and (b) in facilitating new bone formation in the fractured bone and its surroundings.

The bioabsorbable screws of the EXAMPLE 3 with the maximum thread diameter of 3.5 mm and length of 40 mm can be applied in treatment of different types of cancellous bone fractures and osteotomies in the general fashion described, e.g., in P. Rokkanen, et al. "Absorbable Fixation in Orthopedic Surgery (AFOS), Surgical Technique", Helsinki University, Helsinki, 1996. Principally, the reduced bone components are fixed together with at least one screw, after drilling and tapping for the screw a suitable channel through the bone components.

It is expected that the bioabsorbable, ciprofloxacin-releasing, antibacterial, osteopromoting bioactive glass-containing screws will (a) provide effective release of ciprofloxacin for several weeks into the bone surrounding the screws and (b) facilitate for several weeks or months new bone formation into the area of bone fracture and its surroundings and into the drill hole and (c) express additional antibacterial effect by means of bioabsorbable, bioactive glass particles (spheres) up to several months.

Accordingly, it is expected that the screws of the invention are superior in comparison to prior art screws in the treatment of infected cancellous bone fractures in patients with high risk of infection (like diabetic patients, patients with inferior blood circulation in extremities, patients with poor general condition, old age, alcoholism, or disease lowering the general power of resistance against infections).

The surprisingly advantageous effect of the screws of the present invention in treatment of the described indications originates from four partially overlapping phenomena: (a) strong fixation of a bone fracture or osteotomy with a strong self-reinforced screw, (b) rapid and long-lasting release of antibiotic in a concentration high enough for treatment and/or prevention of infection, (c) rapid and long-lasting dissolution of bioactive glass and precipitation of hydroxyapatite into the surroundings of the bioactive glass particles, facilitating new bone formation into a fracture area, its surroundings and into the drill hole, and (d) long-lasting antibacterial effect also originating from the dissolution of bioactive glass.

It is natural that the geometry of the fixation implants of the invention is not limited to screws. Other bone and soft tissue fixation implants can be manufactured according to the invention.

After the description above of the present invention and certain specific embodiments thereof, it will be readily apparent to those skilled in the art that many variations and modifications may be made to the present invention without departing from the spirit and scope thereof.

We claim:

1. A synthetic bioabsorbable drug-delivery material comprising:

a synthetic bioabsorbable polymeric matrix;

a ciprofloxacin antibiotic phase dispersed into said polymeric matrix; and antibacterial, bioabsorbable, bioactive glass dispersed into said polymeric matrix for the promotion of bone growth.

2. The drug delivery material of claim 1, wherein the material is in the form of microspheres, spheres, capsules, tablets, pearls, pearls in string, beads, membranes, films, fibers, filaments, threads, cords or knitted or woven fiber fabrics.

3. The drug delivery material of claim 1, wherein said antibiotic phase comprises from 1 to 20 weight percent of said material.

4. The drug delivery material of claim 1, wherein at least a portion of said material is porous.

5. The drug delivery material of claim 4, wherein the surface of said material is porous.

6. The drug delivery material of claim 1, wherein said bioactive glass is released from said material for a period of at least 4 weeks in in vivo conditions.

7. The drug delivery material of claim 1 wherein said antibiotic phase is released at a level of at least 2 mg/l after 4 weeks in in vivo conditions.

8. The drug delivery material of claim 1 wherein said bioactive glass is in the form of fibers.

9. The drug delivery material of claim 8 wherein said fibers reinforce said material.

10. The drug delivery material of claim 1, wherein the material is self-reinforced through solid state deformation.

11. A surgical implant comprising the material of claim 1.

12. The implant of claim 11, wherein the implant is in the form of a pin, screw, plate, tack, intramedullary nail, bolt, suture anchor, tissue anchor, interference screw, arrow, or wedge.

13. The implant of claim 11, wherein said material is a coating on the surface of said implant.

14. A method of treating osteomyelitis or bone infection in a bone comprising:

providing a synthetic bioabsorbable drug-delivery surgical implant of claim 11; and inserting said implant in said bone.

15. The method of treating osteomyelitis or bone infection in a bone comprising:

providing a material of claim 1; and applying said material to said bone.

* * * * *